Figure 1:
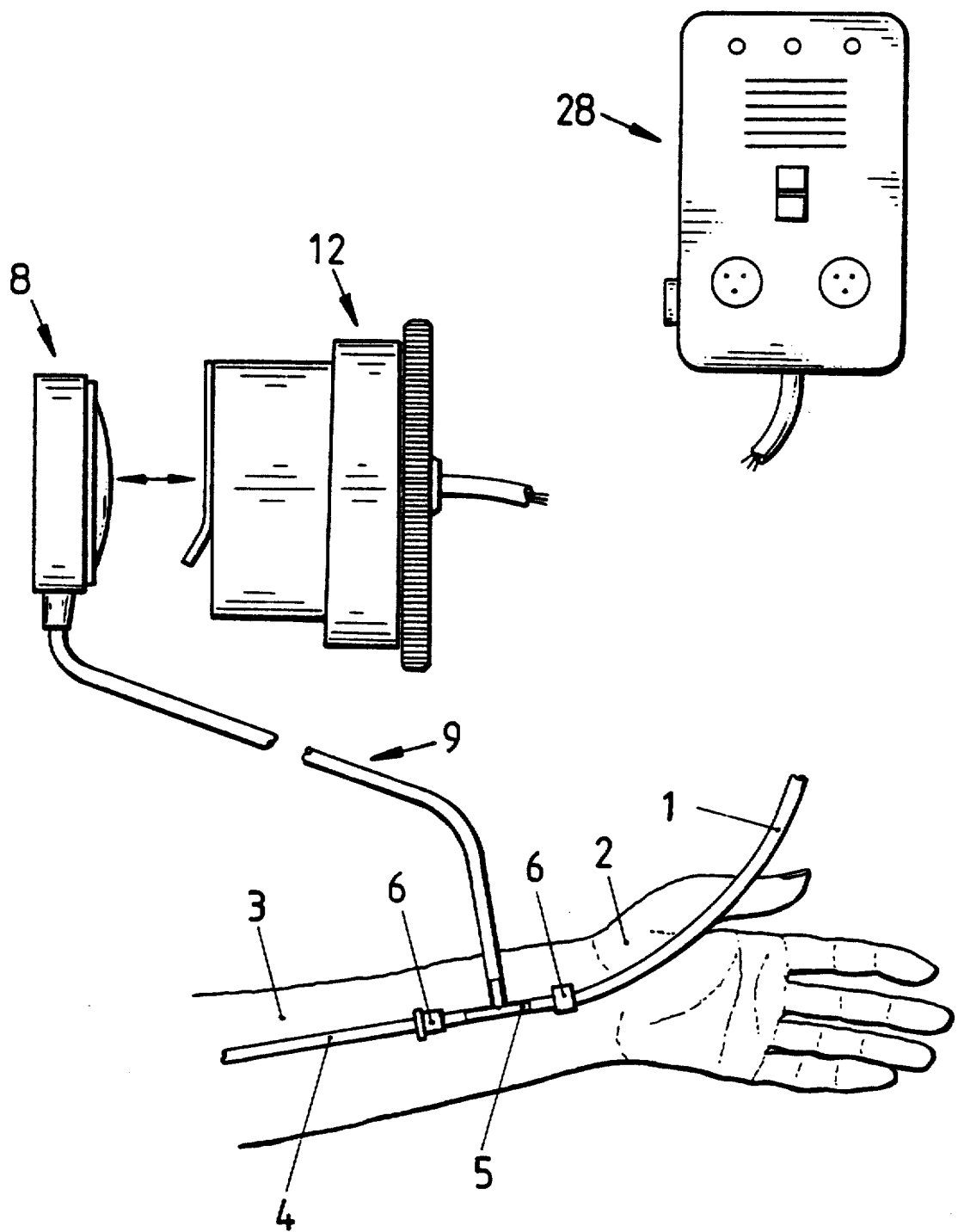

United States Patent [19]

Mokros

[11] Patent Number: 4,994,035
[45] Date of Patent: Feb. 19, 1991

[54] PRESSURE-TRANSMITTING DIAPHRAGM SYSTEM FOR INFUSIONS

[76] Inventor: Klaus Mokros, Brentanostrasse 51, D-8755 Alzenau, Fed. Rep. of Germany

[21] Appl. No.: 345,080

[22] Filed: Apr. 28, 1989

[30] Foreign Application Priority Data

May 11, 1988 [DE] Fed. Rep. of Germany ....... 3816128

[51] Int. Cl.$^5$ .............................................. A61M 1/00
[52] U.S. Cl. .................................. 604/118; 128/675; 200/83 J; 604/65
[58] Field of Search ...................... 604/31, 50, 65, 66, 604/67, 118; 128/675; 200/83 J

[56] References Cited

U.S. PATENT DOCUMENTS

| | | | |
|---|---|---|---|
| 3,158,028 | 1/1968 | Chope | 128/675 X |
| 3,418,853 | 12/1968 | Curtis | 128/675 X |
| 3,738,356 | 6/1973 | Workman | 128/675 |
| 4,185,641 | 1/1980 | Minior et al. | 128/675 |
| 4,227,420 | 10/1980 | Lamadrid | 128/675 X |
| 4,261,360 | 4/1981 | Perez | 604/31 |
| 4,277,227 | 7/1981 | Jenkins | 417/63 |
| 4,282,881 | 8/1981 | Todd et al. | 128/675 X |
| 4,398,542 | 8/1983 | Cunningham et al. | 128/675 |
| 4,591,677 | 5/1986 | Hirota et al. | 200/835 |
| 4,825,876 | 5/1989 | Beard | 128/675 |
| 4,886,498 | 12/1989 | Newton | 604/118 |

FOREIGN PATENT DOCUMENTS

| | | | |
|---|---|---|---|
| 3108767 | 9/1982 | Fed. Rep. of Germany | 128/675 |
| WO8202657 | 8/1982 | World Int. Prop. O. | 128/675 |

Primary Examiner—John D. Yasko
Assistant Examiner—Adam J. Cermak
Attorney, Agent, or Firm—Max Fogiel

[57] ABSTRACT

A pressure-transmitting diaphragm system for infusions, especially for infusions supplied by a pressure-generating pump, with an infusion line leading from the infusion receptacle to the catheter and with a pressure transducer that operates in conjunction with a pressure sensor to activate a signal generator.

The object of the present invention is to provide a pressure-transmitting diaphragm system for infusions of the aforesaid type that can be employed with different types of infusion system and will immediately indicate excessive pressure in the infusion line, especially when it is occasioned by an obstructed or displaced catheter.

A closed pressure line (9) communicates with both the infusion line (1) and the pressure transducer (8).

11 Claims, 3 Drawing Sheets

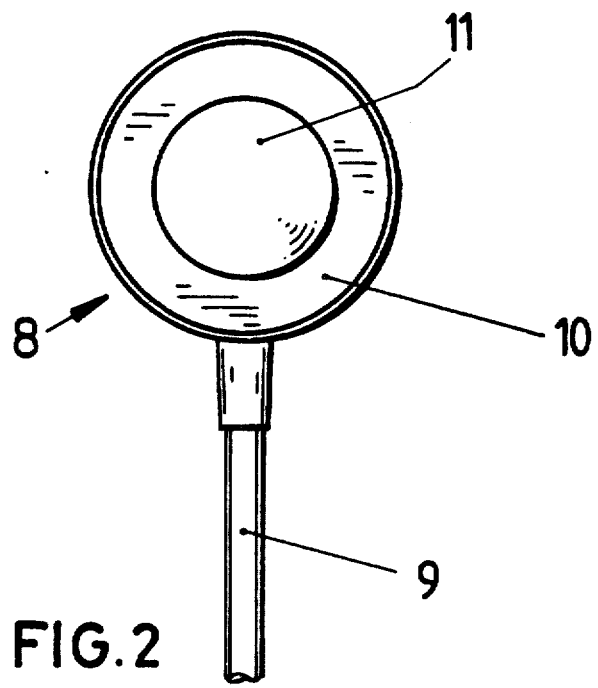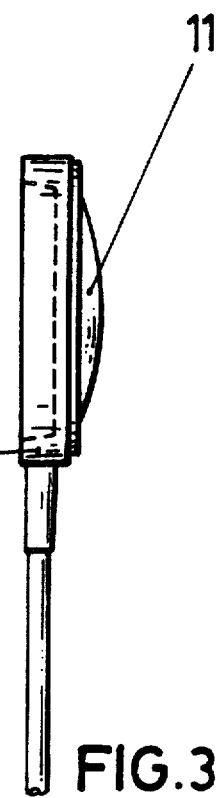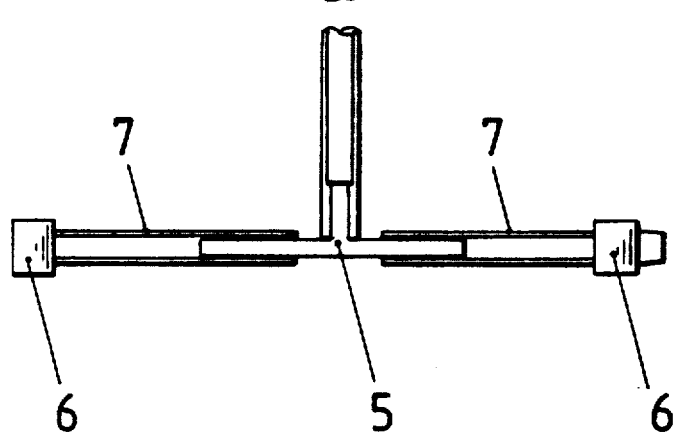

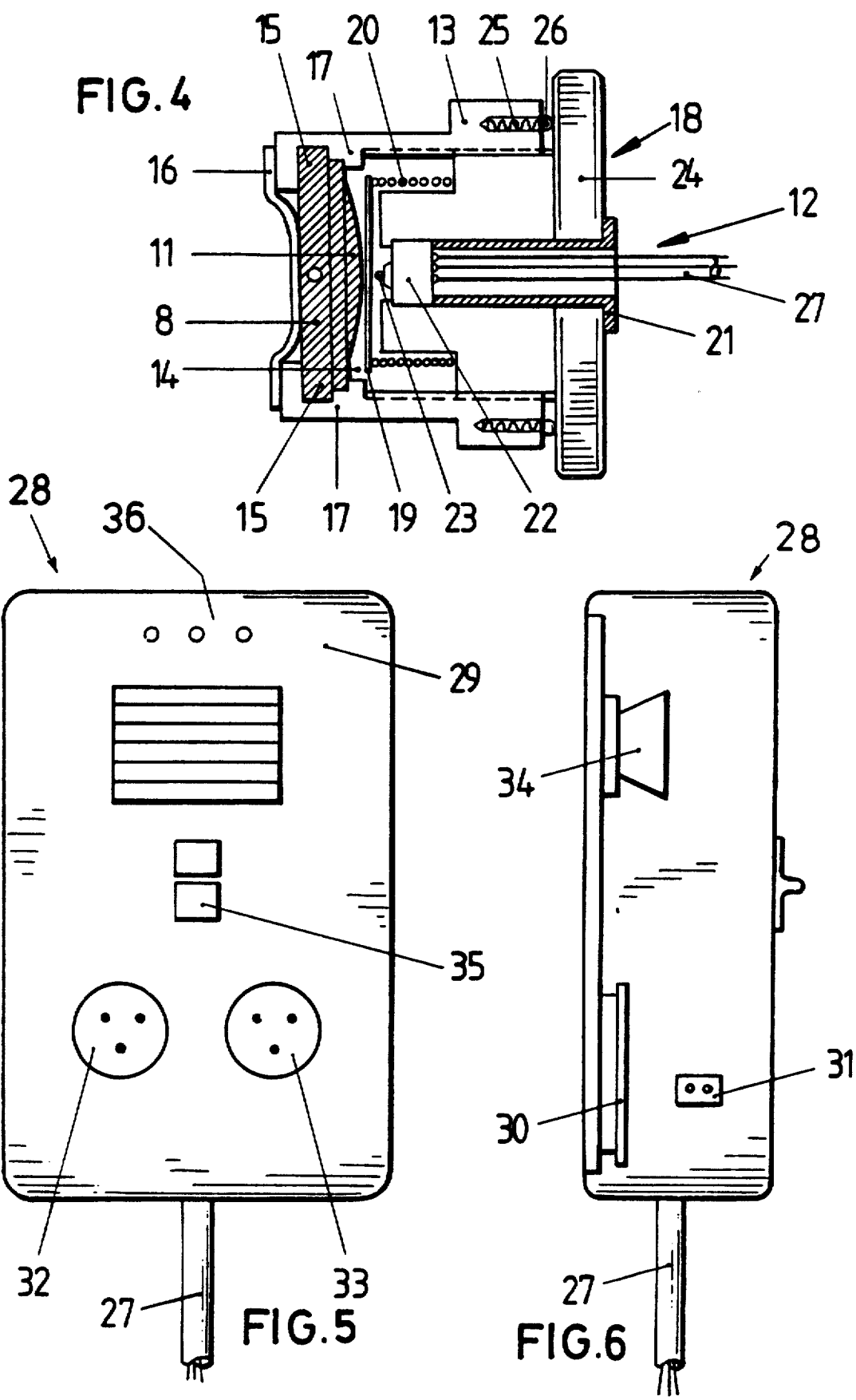

PRESSURE-TRANSMITTING DIAPHRAGM SYSTEM FOR INFUSIONS

The invention concerns a pressure-transmitting diaphragm system for infusions, especially for infusions supplied by a pressure-generating pump, with an infusion line leading from the infusion receptacle to the catheter and with a pressure transducer that operates in conjunction with a pressure sensor to activate a signal generator.

The purpose of excessive-pressure alarm systems for infusions is to indicate the presence of impermissible pressures in the infusion system that might injure the patient. The catheter can become obstructed or displaced during the infusion procedure, and excessive pressure build up in the line leading to the catheter as the pump continues to supply infusion to it, even though none arrives at the patient. If blood-pressure controlling agents are being infused for example, any interruption in the supply will obviously have an immediate negative effect on the body's mechanism of regulation. An excessive-pressure alarm system for infusions must accordingly be expected to emit a signal indicating the presence of the situation as soon as possible after it occurs.

Infusion systems that operate in a wide range of ways are known from practice. They employ a pressure-transmitting diaphragm system of the aforesaid type, which, however, responds late, usually as the result of its design. Inserting a syringe containing the infusion in a pump that applies force to the syringe's plunger by way of a spindle or rack and pinion for example is known. The spindle is designed to control the flow of the infusion in minimum increments and as precisely as possible while advancing as slowly as possible. A pressure transducer is positioned between the spindle and the plunger and activates a signal generator when the force on the plunger becomes impermissibly high. One drawback to this infusion system is that the alarm system activates only when the pressure sensor detects excessive pressure in the vicinity of the pump. Another is that, since the pressure sensor is located in the operating range of the spindle and plunger, the force on the plunger and the pressure transmitted to the pressure sensor superimpose, contaminating the results due to the relative variations in pressure detected by the sensor. Experience has demonstrated that, when the infusion line becomes obstructed and an excessive pressure of 0.6 to sometimes more than 5 bars must be attained before the pressure transducer and the pressure sensor will activate the signal generator, vital minutes can elapse before a signal indicating the situation is emitted.

Positioning the pressure transducer directly adjacent to the pump in the line leading to the catheter is also known from another type of infusion system that employs a constricted-tube pump. The pressure transducer in this infusion system generates a signal that is compared with a prescribed threshold at a specific point of time in the pumping cycle to indicate excessive pressure in the infusion line. One drawback to this infusion system is that the alarm system, especially the pressure transducer, can be employed only in conjunction with a constricted-tube pump. Another is that the pressure transducer must be positioned near the pump in order to prevent feedback to it, and specifically in the infusion line that constantly has infusion traveling through it.

The object of the present invention is to provide a pressure-transmitting diaphragm system for infusions of the aforesaid type that can be employed with different types of infusion system and will immediately indicate excessive pressure in the infusion line, especially when it is occasioned by an obstructed or displaced catheter.

This object is attained in accordance with the invention in a pressure-transmitting diaphragm system for infusions of the aforesaid type characterized by a closed pressure line that communicates with both the infusion line and the pressure transducer.

The pressure-transmitting diaphragm system for infusions in accordance with the invention accordingly measures the pressure in the infusion system with a pressure transducer that is positioned in a separate pressure line. No infusion flows through the pressure line, and, when the system is functioning properly, the pressure transducer is constantly inactive. The tubing employed for infusions is very small in diameter, and only a little infusion will generally enter the pressure line because the end of the pressure line remote from the infusion line is sealed off by the pressure transducer.

It is of advantage for the pressure line to communicate with the infusion line in the vicinity of the catheter to ensure that the pressure transducer can detect an obstruction in the immediate vicinity of the catheter for example. One simple way of connecting the pressure line to the infusion line is with a T connector. All that is necessary is to connect the pressure line to one arm of the T, and it makes no difference whether there is infusion or air in the pressure line because any increase in pressure would only immediately force the liquid from the infusion line into the pressure line and any decrease in pressure would introduce so little air into the infusion line that the patient would not be threatened.

It is practical for the main component of the pressure transducer to have a connection to the pressure line and accommodate an inflatable, meaning elastic, diaphragm. Since the inside of the diaphragm communicates directly with the pressure line, increasing the pressure in the pressure line will inflate or expand the diaphragm, and the resulting displacement is exploited to activate the pressure sensor. Specifically, it is considered practical for the main component of the pressure transducer to have an annular opening that accommodates the accordingly circular diaphragm. It is especially simple to connect the pressure transducer to the pressure sensor when there is in the main component of the pressure sensor an opening that accommodates the pressure transducer and in which it secured by a spring. The pressure sensor will be especially simple in design when it has a contact plate that the diaphragm in the pressure transducer rests against and that is subjected to force opposite the direction that the diaphragm expands in. If a pressure-sensitive switch or sensor is accommodated in the path of the contact plate inside the pressure sensor, the expansion of the diaphragm can be directly transmitted to the pressure-sensitive switch or sensor by way of the contact plate without involving many components. It is considered a particular advantage for the pressure-sensitive switch or sensor to be secured in a mount that can be adjusted in relation to the main component of the pressure sensor. The adjustable mount makes it possible to vary the sensitivity of the pressure-sensitive switch or sensor. Finally, the signal generator that is activated by the pressure sensor should have electronic circuitry for processing the signal and output terminals to the alarm generator or a computer.

The aforesaid invention provides a pressure-transmitting diaphragm system for infusions that can be employed with different types of infusion system because it relates strictly to the pressure prevailing in the infusion line, although, in contrast to the state of the art, the pressure is not determined by a pressure transducer integrated into the infusion line but by one associated with a pressure line that communicates with the infusion line.

Further characteristics of the invention are described with reference to the figures and recited in the subsidiary claims. All the individual characteristics and all combinations thereof are essential to the invention.

One embodiment of the invention will now be described by way of example but without the invention being restricted to it and with reference to the drawings, wherein FIG. 1 is a schematic illustration of the essential components of a pressure-transmitting diaphragm system for infusions, FIG. 2 is a front view of the pressure sensor and of the pressure line with its connection to the infusion line, FIG. 3 is an edge-on view of the pressure transducer, FIG. 4 is a longitudinal section through the center of the pressure sensor with the pressure transducer inserted in it, FIG. 5 is a view of the front of the signal generator, and FIG. 6 is a side view of the signal generator.

FIG. 1 illustrates only the section in the proximity of a hand 2 of an infusion line 1 that communicates with an unillustrated infusion receptacle. Inserted into an unillustrated vein in a forearm 3 is a catheter 4 that communicates with infusion line 1 by way of a T connector 5 with interlocking male and female Luer's connections. The infusion can accordingly be supplied to the vein through infusion line 1, the arm of T connector 5, and catheter 4. From the aspect of the present invention it makes no difference whether the infusion is supplied to infusion line 1 by way of a pump or directly from an infusion flask.

FIG. 2 illustrates in detail how T connector 5 communicates with straight connectors 6 by way of sections 7 of tubing. FIGS. 2 and 3 also illustrate how a pressure transducer 8 communicates with infusion line 1 and catheter 4 by way of a pressure line 9 that communicates with T connector 5. Pressure transducer 8 consists of a main component 10 with an annular opening that accommodates a circular diaphragm 11 that can be inflated and expanded. Before the infusion procedure is initiated, the section between catheter 4 and the end of infusion line 1 is adjusted with the Luer's connectors. There will be less than 1 ml of air in the relatively short pressure line 9 and in the space between the main component 10 of pressure transducer 8 and diaphragm 11 due to the dimensions of the air space, and that volume will remain relatively constant during the procedure. If catheter 4 becomes obstructed, the pressure in the infusion system and on the infusion in T connector 5 and in infusion line 1 will increase, compressing the air in pressure line 9 and in pressure transducer 8 and expanding diaphragm 11 farther outward. Since such an expansion would also occur of course if there were infusion in pressure line 9 and in pressure transducer 8, diaphragm 11 would also expand sufficiently if it were sensitive enough and if the infusion flask were suspended high enough above the catheter. Obviously, then, the pressure-transmitting diaphragm system in accordance with the invention is not restricted to pumped infusions.

FIG. 4 illustrates how pressure transducer 8 operates in conjunction with a pressure sensor 12. The sensor also consists of a main component 13 that has an opening 14 with two parallel grooves 15 to accommodate the main component 10 of pressure transducer 8, which is secured therein by a spring 16 attached to main component 13. Screwed into main component 13 is a setscrew 18, and a plate 19 rests both against diaphragm 11 and against a compression spring 20 on setscrew 18. Setscrew 18 has a central bore that accommodates, in such a way that it cannot rotate, an adjustable mount 21 for a pressure-sensitive switch 22. The switch has a contact pin 23 positioned slightly away from contact plate 19 and the unexpanded diaphragm 11. Finally, also connected to setscrew 18 such that it cannot rotate in relation to it is a ring 24 for adjusting the sensitivity of the pressure sensor. The surface of the ring that faces main component 13 has a number of unillustrated recesses that accommodate snap-in balls 26 subjected to the force of compression springs 25. Thus, when it expands as the result of increased pressure in pressure line 9, diaphragm 11 will come into contact with plate 19 and displace it against the force of compression spring 20. Once the plate has traveled a specific distance, it will come into contact with pin 23 and activate pressure-sensitive switch 22.

FIG. 4 also illustrates a three-pole cable that is connected to pressure-sensitive switch 22 and leads to the signal generator 28 illustrated in FIGS. 5 and 6. The generator consists essentially of a housing 29 that accommodates an electronic signal-processing circuit 30, a power connection 31, an output terminal 32 for signaling the nurses' station, an output terminal 33, for other alarms or to a computer, a loudspeaker or siren 34, a cable 27 to pressure sensor 12, a power switch 35, and light-emitting diodes 36 to indicate that the device is operating.

Although the aforesaid pressure-transmitting diaphragm system is especially appropriate for detecting undesired excessive pressures during infusions, it is not restricted to that application. It is also possible to employ it to measure blood pressure by providing only one access from catheter 4 to pressure line 9 and clamping off the branch that ordinarily leads to infusion line 1. Fluctuations in blood pressure can then be directly measured and displayed in accordance with the setting of the pressure-sensitive switch.

I claim:

1. A pressure-transmitting diaphragm system for infusions, comprising: a source of infusion substance; a catheter; an infusion line connecting said catheter to said infusion source; a pressure transducer mounted in a pressure sensor; a closed pressure line containing air connected between said infusion line and said pressure transducer, said transducer being removably mounted in said pressure sensor; said pressure sensor having a mounting member with an opening for removably holding said transducer; spring means for securing said transducer in said opening for sterile separation between said transducer and said pressure sensor; and means connected to said pressure sensor for generating a warning alarm signal when pressure in said pressure line exceeds a predetermined threshold, said warning alarm signal having only two states to indicate whether or not said threshold is exceeded.

2. A pressure-transmitting diaphragm system for infusions as defined in claim 1, including a T connector at a junction connecting said catheter with said infusion line and said pressure line.

3. A pressure-transmitting diaphragm system as defined in claim 2, including tubular sections mounted on ends of said T connector and having male and female connectors at ends of said tubular sections connected to said infusion line and said catheter.

4. A pressure-transmitting diaphragm system as defined in claim 1, wherein said pressure transducer has a frame member; an inflatable diaphragm held in said frame member; and means for connecting said frame member to said pressure line.

5. A pressure-transmitting diaphragm system as defined in claim 4, wherein said frame member has a circular opening for holding said diaphragm said diaphragm having a circular shape.

6. A pressure-transmitting diaphragm system as defined in claim 4, including a contact plate in said mounting member of said pressure sensor, said transducer resting against said contact plate, said transducer being subjected to a force opposite the direction of expansion of said diaphragm.

7. A pressure-transmitting diaphragm system as defined in claim 6, including a pressure-sensitive switch inside said mounting member of said pressure sensor, said contact plate having a path of motion; said pressure-sensitive switch being located in said path of motion of said contact plate.

8. A pressure-transmitting diaphragm system as defined in claim 7, including means for mounting said pressure-sensitive switch and being adjustable relative to said mounting member of said pressure sensor.

9. A pressure-transmitting diaphragm system as defined in claim 1, including signal generating means connected to said pressure sensor and having electronic circuits for processing a signal generated when pressure in said pressure line exceeds a predetermined level; and alarm generator means connected to said signal generator means for providing an alarm when pressure in said pressure line has exceeded said predetermined threshold.

10. A pressure-transmitting diaphragm system as defined in claim 1, including signal generator means connected to said pressure sensor and having electronic circuit means for processing a signal when pressure in said pressure line exceeds a predetermined threshold; and computer means connected to said signal generator means for receiving said processed signal.

11. A pressure-transmitting diaphragm system for infusions, comprising: a source of infusion substance; a catheter; an infusion line connecting said catheter to said infusion source; a pressure transducer mounted in a pressure sensor; a closed pressure line containing air connected between said infusion line and said pressure transducer, said transducer being removably mounted in said pressure sensor; said pressure sensor having a mounting member with an opening for removably holding said transducer; spring means for securing said transducer in said opening for sterile separation between said transducer and said pressure sensor; and means connected to said pressure sensor for generating a warning alarm signal when pressure in said pressure line exceeds a predetermined threshold, said warning alarm signal having only two states to indicated whether or not said threshold is exceeded; a T connector at a junction connecting said catheter with said infusion line and said pressure line; tubular sections on ends of said T connector and having male and female connectors at ends of said sections connected with said catheter and said infusion line; a transducer mounting member connected to said pressure line; an inflatable diaphragm held by said transducer mounting member; said transducer mounting member having a circular opening for holding said diaphragm, said diaphragm having a circular shape; a contact plate in said pressure sensor, said diaphragm resting against said contact plate, said contact plate being subjected to a force opposite to the direction of expansion of said diaphragm; a pressure-sensitive switch in said mounting member of said pressure sensor, said contact plate having a path of motion; said pressure-sensitive switch being located in said path of motion of said contact plate; switch mounting means for mounting said pressure-sensitive switch and being adjustable relative to said mounting member of said pressure sensor; signal generator means connected to said pressure sensor for providing a signal when pressure in said pressure line exceeds a predetermined threshold; said signal generator means having electronic circuit means for processing said signal; an alarm generator means for receiving said signal from said signal generator means to provide an alarm when pressure in said pressure line exceeds said predetermined threshold.

* * * * *